United States Patent [19]

Marhold et al.

[11] 4,331,613
[45] May 25, 1982

[54] PROCESS FOR THE PREPARATION OF TRIFLUOROMETHYLNAPHTHALENES

[75] Inventors: Albrecht Marhold, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 161,810

[22] Filed: Jun. 23, 1980

[30] Foreign Application Priority Data

Jul. 17, 1979 [DE] Fed. Rep. of Germany ....... 2928745

[51] Int. Cl.³ .................... C07C 21/00; C07C 21/18
[52] U.S. Cl. ........................... 260/544 B; 260/544 P; 260/544 F; 260/543 R; 260/543 H; 260/456 R; 568/41; 568/46; 568/49; 568/56; 568/67; 568/631; 568/632; 568/928; 568/929; 570/129; 570/144; 570/164; 570/165
[58] Field of Search ............... 570/170, 129, 144, 164, 570/168; 260/543 R, 544 B, 544 P, 544 F, 543 H, 456 R; 568/67, 41, 46, 49, 56, 631, 632, 928, 929

[56] References Cited

U.S. PATENT DOCUMENTS 2,273,922  2/1942  Benning et al. .................... 570/129

Primary Examiner—Paul J. Killos
Attorney, Agent, or Firm—Sprung, Horn, Kramer & Woods

[57] ABSTRACT

A process for the preparation of an optionally substituted trifluoromethyl-naphthalene which comprises contacting a compound of the formula

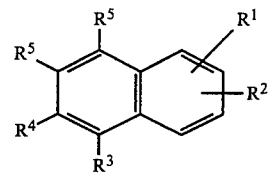

in which $R^1$ denotes hydrogen, alkyl, aralkyl, aryl, aryloxy, arylthio, polyhalogenoalkoxy, polyhalogenoalkylthio, halogen, nitro, halogenocarbonyl, halogenosulphonyl, alkylsulphonyl or arylsulphonyl, it being possible for the aromatic nuclei contained in the substituents $R^1$ to be in turn substituted by halogen, alkyl, polyhalogenoalkoxy or polyhalogenoalkylthio, $R^2$ represents hydrogen, halogen or alkyl and $R^3$, $R^4$, $R^5$ and $R^6$ denote hydrogen, or $R^3$ and $R^4$ or $R^4$ and $R^5$ in each case together denote a fused-on aromatic ring, and wherein, in the case where $R^3$ and $R^4$ together form a fused-on aromatic ring, $R^5$ and $R^6$ independently of one another can also denote, in addition to hydrogen, halogen, nitro, halogenocarbonyl or halogenosulphonyl, and wherein, in the case where $R^4$ and $R^5$ together form a fused-on aromatic ring, $R^3$ and $R^6$ independently of one another can also denote, in addition to hydrogen, halogen, nitro, halogenocarbonyl or halogenosulphonyl, with carbon tetrachloride and hydrogen fluoride at a temperature of 70° to 120° C. and under a pressure of 5 to 30 bars the reaction product then optionally being treated with catalyst activated hydrogen.

14 Claims, No Drawings

PROCESS FOR THE PREPARATION OF TRIFLUOROMETHYLNAPHTHALENES

The invention relates to a process for the preparation of optionally substituted trifluoromethyl-naphthalenes.

It is known from U.S. Pat. No. 2,432,393, to prepare 1-trifluoromethyl-naphthalene by reacting 1-trichloromethyl-naphthalene with antimony trifluoride. The disadvantage of this process is that the 1-trichloromethyl-naphthalene required as the precursor is not accessible in a simple manner from methylnaphthalene by chlorination since the reaction of methylnaphthalene with chlorine to a large extent gives products which are chlorinated in the nucleus (Chem. Ber. 24, 3921 (1891)). It is known, from Zh. Org. Khim. (English translation) 8, 838 (1972), to convert a carboxyl group bonded to the naphthalene nucleus into the trifluoromethyl group by reaction with sulphur tetrafluoride. In the case of the unsubstituted 1-naphthalenecarboxylic acid, this process gives a yield of 7%. Furthermore, it is known from U.S. Pat. No. 2,273,922, to react naphthalene with carbon tetrachloride and hydrogen fluoride in the presence of copper at 150° to 155° C. in a reaction lasting 48 hours. According to the patent claim, trifluoromethyl-naphthalene is said to be obtained in this process. In this U.S. Pat. No. 2,273,922, two reaction products are described, and of these, one is said to have a molecular weight of over 500 and its structure is not described in more detail, while the other is said to be a monotrifluoromethyl-naphthalene with a melting point of 92° C. According to our own observations, this melting point is not even approximately correct for 1-trifluoromethyl-naphthalene or for 2-trifluoromethyl-naphthalene.

A process has now been found for the preparation of optionally substituted trifluoromethyl-naphthalenes, which is characterized in that a compound of the formula

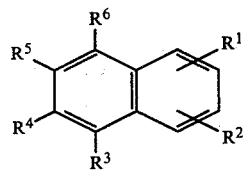

(I)

in which

R$^1$ denotes hydrogen, alkyl, aralkyl, aryl, aryloxy, arylthio, polyhalogenoalkoxy, polyhalogenoalkylthio, halogen, nitro, halogenocarbonyl, halogenosulphonyl, alkylsulphonyl or arylsulphonyl, it being possible for the aromatic nuclei contained in the substituents R$^1$ to be in turn substituted by halogen, alkyl, polyhalogenoalkoxy or polyhalogenoalkylthio, R$^2$ represents hydrogen, halogen or alkyl and R$^3$, R$^4$, R$^5$ and R$^6$ denote hydrogen, or R$^3$ and R$^4$ or R$^4$ and R$^5$ in each case together denote a fused-on aromatic ring, and wherein, in the case where R$^3$ and R$^4$ together form a fused-on aromatic ring, R$^5$ and R$^6$ independently of one another can also denote, in addition to hydrogen, halogen, nitro, halogenocarbonyl or halogenosulphonyl, and wherein, in the case where R$^4$ and R$^5$ together form a fused-on aromatic ring, R$^3$ and R$^6$ independently of one another can also denote, in addition to hydrogen, halogen, nitro, halogenocarbonyl or halogenosulphonyl, is reacted with carbon tetrachloride and hydrogen fluoride at a temperature of 70° to 120° C. and under a pressure of 5 to 30 bars, and the reaction product is optionally further reacted with catalytically activated hydrogen.

Examples of alkyl which may be mentioned are straight-chain or branched hydrocarbon radicals with 1 to 8 carbon atoms, such as methyl, ethyl, propyl, butyl, hexyl or octyl, preferably those with 1–4 carbon atoms and particularly preferably methyl.

Examples of aralkyl which may be mentioned are hydrocarbon radicals with 1 or 2 carbon atoms in the aliphatic part and 6 to 12 carbon atoms in the aromatic part, such as benzyl, phenylethyl, diphenylmethyl, diphenylethyl or naphthylmethyl, preferably benzyl.

Examples of aryl which may be mentioned are aromatic hydrocarbon radicals with 6 to 12 carbon atoms, such as phenyl, diphenyl or naphthyl, preferably phenyl.

Examples of aryloxy which may be mentioned are radicals with 6 to 12 carbon atoms, such as phenyloxy, diphenyloxy or naphthyloxy, preferably phenyloxy.

Examples of arylthio which may be mentioned are radicals with 6 to 12 carbon atoms, such as phenylthio, diphenylthio or naphthylthio, preferably phenylthio.

Examples of polyhalogenoalkoxy whose may be mentioned are radicals which have 1 to 4 carbon atoms and are substituted by fluorine, chlorine or bromine, such as trifluoromethoxy, trichloromethoxy, tribromomethoxy, difluorochloromethoxy, difluorobromomethoxy, fluorodichloromethoxy, fluorodibromomethoxy, dibromochloromethoxy, bromodichloromethoxy, pentafluoroethoxy, pentachloroethoxy, pentabromoethoxy, α-difluoro-β-fluoro-β-chloroethoxy, propoxy radicals which are halogenated by the same or different halogens or butoxy radicals which are halogenated by the same or different halogens. Polyhalogenoalkoxy radicals with 1 to 2 carbon atoms are preferred, and methoxy radicals halogenated by the same or different halogens are very particularly preferred.

Examples of polyhalogenoalkylthio which may be mentioned are those such as are mentioned as polyhalogenoalkoxy radicals, but in which a sulphur atom takes the place of the oxygen atom. They can have 1 to 4 carbon atoms, preferably 1 to 2 carbon atoms or particularly preferably 1 carbon atom.

Halogen which may be mentioned is, for example, fluorine, chlorine, bromine or iodine, preferably fluorine, chlorine or bromine and very particularly preferably chlorine.

Examples of halogenocarbonyl which may be mentioned are fluorocarbonyl, chlorocarbonyl or bromocarbonyl, preferably chlorocarbonyl.

Examples of halogenosulphonyl which may be mentioned are fluorosulphonyl, chlorosulphonyl or bromosulphonyl, preferably chlorosulphonyl.

Examples of alkylsulphonyl which may be mentioned are sulphonyl radicals with $C_1$–$C_4$-alkyl groups, such as methylsulphonyl, ethylsulphonyl, propylsulphonyl, isopropylsulphonyl, butylsulphonyl or isobutylsulphonyl, preferably methylsulphonyl and ethylsulphonyl.

Examples of arylsulphonyl which may be mentioned are sulphonyl groups with $C_6$ to $C_{12}$-aryl groups, such as phenylsulphonyl, diphenyl-sulphonyl or naphthylsulphonyl, preferably phenylsulphonyl.

The aromatic nuclei contained in the substituents can in turn be substituted by halogen, $C_1$–$C_4$-alkyl, $C_1$–$C_4$-polyhalogenoalkoxy or $C_1$–$C_4$-polyhalogenoalkylthio.

The radicals $R^3$ and $R^4$ or $R^4$ and $R^5$ can in each case together denote a fused-on aromatic ring, so that compounds of the phenanthrene or anthracene series can be formed.

Preferred compounds within the scope of the formula (I) are compounds of the formula

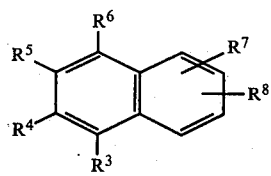

(II)

in which $R^7$ denotes aryloxy, arylthio, polyhalogenoalkoxy, polyhalogenoalkylthio, halogen, nitro, halogenocarbonyl, halogenosulphonyl, alkylsulphonyl or arylsulphonyl, it being possible for the aromatic nuclei contained in the substituent $R^7$ to be in turn substituted by halogen, alkyl, polyhalogenoalkoxy or polyhalogenoalkylthio, $R^8$ represents hydrogen or halogen and $R^3$ to $R^6$ have the meaning indicated above.

Particularly preferred compounds within the scope of the formula (I) are naphthalenes of the formula

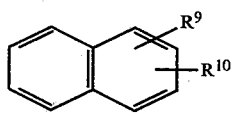

(III)

in which $R^9$ denotes halogen, nitro, halogenocarbonyl or halogenosulphonyl and $R^{10}$ represents hydrogen or halogen.

Very particularly preferred compounds within the scope of the formula (I) are naphthalenes of the formula

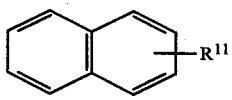

in which $R^{11}$ denotes chlorocarbonyl or chlorosulphonyl.

Examples of compounds of the formulae (I), (II) and (III) which may be mentioned are: naphthalene, 1-chloronaphthalene, 2-chloronaphthalene, 1-naphthalenecarboxylic acid chloride, 2-naphthalenecarboxylic acid chloride, 1-naphthalenesulphonic acid chloride, 2-naphthalenesulphonic acid chloride, 1-nitronaphthalene, 2-nitronaphthalene, 1,4-dichloronaphthalene, 1-nitro-4-methylnaphthalene, 1-nitro-2,3-dimethylnaphthalene, 1-nitro-2,6-dimethylnaphthalene, 1-bromonaphthalene, 1-methyl-4-chlorosulphonyl-naphthalene, 1-chloro-4-methylnaphthalene, 9,10-dichloroanthracene, 1-bromonaphthalene, 2-bromonaphthalene, 1-methylnaphthalene, 1-ethylnaphthalene, 1-butylnaphthalene, 2-methylnaphthalene, 2-ethylnaphthalene, 2-propylnaphthalene, 1-trichloromethoxynaphthalene and 1-pentabromoethylthio-naphthalene.

carbon tetrachloride is employed in the process according to the invention in an amount of, for example, 3 to 20 mols, preferably 6 to 12 mols, per mol of the compound of the formula (I).

Hydrogen fluoride is employed in the process according to the invention in an amount of, for example, 3 to 60 mols, preferably 5 to 50 mols, per mol of the compound of the formula (I).

If carbon tetrachloride or hydrogen fluoride are employed in amounts smaller than those indicated, there is the danger of a decrease in yield due to incomplete reaction. For economic reasons, the use of an amount of carbon tetrachloride or hydrogen fluoride greater than the amount indicated is not very appropriate.

The process according to the invention is carried out, for example, at a temperature of 70° to 120° C, preferably of 80° to 120° C. and particularly preferably of 90° to 110° C.

The process according to the invention is carried out under increased pressure. A pressure of 5 to 30 bars, preferably 10 to 20 bars, may be mentioned as an example of an increased pressure. This pressure can be achieved, for example, by the autogenous pressure of the reaction components employed and of the reaction components formed. However, it is also possible to establish the chosen pressure by means of compressed air from the atmosphere or by means of a compressed inert gas, for example nitrogen.

The process of this invention can be carried out in the absence of a catalyst, in particular the process is carried out in the absence of copper or a copper compound.

In the case where several isomeric reaction products are formed by the reaction, according to the invention, of a compound of the formula (I) with carbon tetrachloride and hydrogen fluoride, it can be desirable to remove completely or partly the substituent or substituents originally present in the compound of the formula (I) by reaction with catalytically activated hydrogen in the presence of an alkaline substance in order thus to reduce the number of isomeric, optionally substituted trifluoromethyl-naphthalenes.

In this variant of the process according to the invention, compounds of the formula

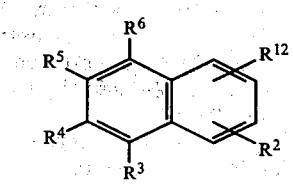

(IV)

in which $R^2$ to $R^6$ have the abovementioned meaning and $R^{12}$ denotes chlorine or bromine, are preferably employed.

Thus, for example, in the reaction, according to the invention, of 1-chloro-naphthalene according to the equation

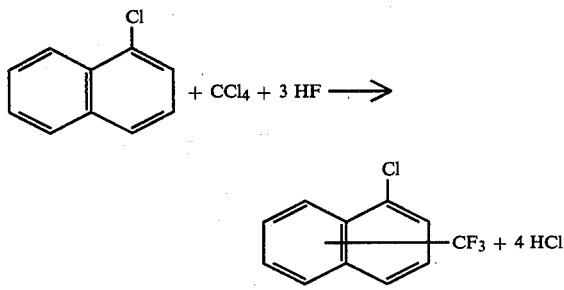

1-chloro-4-trifluoromethyl-naphthalene and/or 1-chloro-5-trifluoromethyl-naphthalene and/or 1-chloro-8-trifluoromethyl-naphthalene are formed as the main products. 1-Trifluoromethyl-naphthalene is obtained as a single compound in high yield by dechlorination of the said isomers, which is carried out, according to the invention, by treatment with catalytically activated hydrogen in the presence of an alkaline substance.

Examples of catalysts which may be mentioned for catalytic activation of the hydrogen are those of the Raney type, such as Raney nickel, Raney iron/nickel, Raney copper/nickel or Raney cobalt/nickel. Raney nickel is preferably used.

The reaction with catalytically activated hydrogen is carried out in a solvent suitable for catalytic hydrogenations, for example in methanol, ethanol or dioxane. 20° to 60° C., preferably 30° to 50° C., may be mentioned as an example of the temperature for the hydrogenation.

For the reaction, according to the invention, with catalytically activated hydrogen, a hydrogen pressure of 25 to 70 bars, preferably 30 to 50 bars, may be mentioned by way of example.

The hydrogenation according to the invention is carried out in the presence of an alkaline compound, such as sodium hydroxide, potassium hydroxide, sodium carbonate potassium carbonate, sodium bicarbonate or potassium bicarbonate, preferably sodium hydroxide or potassium hydroxide. The alkaline substance is employed in an amount of 1.1 to 3, preferably 1.2 to 2, equivalents per equivalent of the substituent to be removed from the trifluoromethyl-naphthalene.

Compounds of the formula

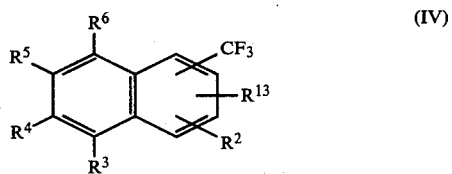

in which $R^2$ to $R^6$ have the meaning indicated above and $R^{13}$ denotes hydrogen, alkyl, aralkyl, aryl, aryloxy, arylthio, polyfluoroalkoxy, polyfluoroalkylthio, halogen, nitro, fluorocarbonyl, fluorosulphonyl, alkylsulphonyl or arylsulphonyl, it being possible for the aromatic nucleus contained in the substituent $R^{13}$ to be in turn substituted by halogen, alkyl, polyfluoroalkoxy or polyfluoroalkylthio, can be prepared with the aid of the process according to the invention.

Examples of compounds of the formula (IV) are: 1-trifluoromethylnaphthalene, 2-trifluoromethylnaphthalene, 5-trifluoromethyl-naphthalene-1-carboxylic acid fluoride, 5-trifluoromethyl-naphthalene-2-carboxylic acid fluoride, 5-nitro-1-trifluoromethylnaphthalene, 5-trifluoromethylnaphthalene-1-sulphonic acid fluoride, 5-trifluoromethylnaphthalene-2-sulphonic acid fluoride, 5-trifluoromethyl-1-methylsulphonyl-naphthalene and 1-trifluoromethyl-9,10-dichloro-anthracene.

The process according to the invention can be carried out, for example, as follows:

Anhydrous liquid hydrogen fluoride is initially introduced into a stainless steel autoclave, whilst cooling and a solution of the naphthalene of the formula (I) in carbon tetrachloride is added. A pressure of about 3 bars is then established with nitrogen and the contents of the autoclave are brought to the desired reaction temperature, whilst stirring. After a short time, the start of the reaction manifests itself by the rise in pressure as a result of the hydrogen chloride formed. This hydrogen chloride is let down, continuously or at intervals, via a reflux condenser which has a regulating valve and is cooled with brine. When the reaction has ended, the excess hydrogen fluoride and the excess carbon tetrachloride are distilled off and the reaction product is isolated by methods which are in themselves known, for example by distillation or crystallization.

In the case where further reaction of the reaction product with catalytically activated hydrogen is envisaged, the crude reaction product, dissolved in a suitable solvent, for example methanol, is initially introduced into a hydrogenation apparatus. The alkaline substance and the Raney catalyst are added and a hydrogen pressure of about 30 to 50 bars is maintained at a reaction temperature of about 30° to 50° C. until saturation conditions are reached. When the hydrogenation has ended, the reaction mixture is stirred into water, the catalyst is filtered off and the reaction product is worked up from the organic phase, which has separated out, by customary methods of working up, for example crystallization or distillation.

The process according to the invention enables the trifluoromethyl group to be introduced into naphthalene derivatives in only one reaction step and with a high yield in a manner which represents a technical advance, whilst the processes according to the state of the art are multi-stage processes or give products which are not clearly defined.

It is surprising that it is possible to carry out the process according to the invention smoothly, since it could be expected that naphthalene derivatives would mainly undergo uncontrolled condensation reactions and resinification reactions in the presence of a chloroalkyl compound, such as carbon tetrachloride, and in the presence of a Friedel-Crafts catalyst, such as hydrogen fluoride, as is known from Organicum, Organisch-chemisches Grundpraktikum (Basic Manual of Organic Chemistry), 8th edition, VEB-Verlag, Berlin 1968, page 302, for the reaction of benzene with carbon tetrachloride in the presence of aluminium chloride.

The optionally substituted trifluoromethyl-naphthalenes which can be prepared by the process according to the invention are important intermediate products for dyestuffs and insecticides. Thus, for example, nitro-trifluoromethyl-naphthalene can be reduced to amino-trifluoromethyl-naphthalene. Diazotization of the latter and coupling of the diazotization product with dimethylaniline gives a dyestuff, the absorption maximum of which is shifted into a spectral region of longer wavelength compared with the dyestuff which is analogous but derived from p-amino-benzotrifluoride (Zh. Org. Khim. (English translation) 8, 838 (1972)).

EXAMPLE 1

1,600 ml of anhydrous hydrogen fluoride are initially introduced at 10° C. into a 5 l stirred autoclave of high-grade steel, and 750 g of 1-chloro-naphthalene, dissolved in 1,900 ml of carbon tetrachloride, are then added. Nitrogen is now forced in to a pressure of about 3 bars and the reaction mixture is heated to a temperature of 100° to 105° C., whilst stirring. Hydrogen chloride is evolved and is let down at 16 bars via a reflux condenser cooled to −10° C. and via a regulating valve. The reaction is allowed to proceed under these conditions for 8 hours and the autoclave is then cooled. After letting down, first the excess hydrogen fluoride and then the excess carbon tetrachloride are distilled off from the reaction batch. Distillation under reduced pressure gives 807 g of an isomer mixture of 1-chloro-trifluoromethyl-naphthalene. Boiling point: 120° to 130° C./15 mm Hg; $n_D^{20}$: 1.5540.

200 g of the isomeric 1-chloro-trifluoromethyl-naphthalenes, dissolved in 800 ml of methanol, are initially introduced into a hydrogenation apparatus. 52 g of sodium hydroxide and 20 g of Raney nickel are added and the reaction batch is warmed to 40° C. Hydrogenation is then carried out under a hydrogen pressure of 40 bars, until the batch is saturated by hydrogen. After cooling and letting down, the reaction mixture is stirred into 500 ml of water, the catalyst is filtered off and the organic phase which has settled out is separated off. After drying the organic phase over sodium sulphate and distilling it under reduced pressure, 147 g of 1-trifluoromethyl-naphthalene, which is liquid at room temperature, are obtained; boiling point: 102° to 104° C./16 mm Hg; $n_D^{20}$: 1.5362.

EXAMPLE 2

500 ml of hydrogen fluoride, 600 ml of carbon tetrachloride and 128 g of naphthalene are reacted at 105° C. and under 15 bars for 4 hours, as described in Example 1. After working up the batch by distillation, 50 g of a product which has a boiling point of 70° to 80° C./3 mm Hg and, according to the $F^{19}$ spectrum, consists of 1-trifluoromethylnaphthalene to the extent of 40% by weight and of 2-trifluoromethylnaphthalene to the extent of 60% by weight, are obtained.

EXAMPLE 3

400 g of 1-naphthalenecarboxylic acid chloride are reacted in 1,800 ml of carbon tetrachloride and 1,800 ml of hydrogen fluoride at 109° C. and under 17 bars for 6½ hours, analogously to Example 1. After distillation of the batch, 370 g of 5-trifluoromethyl-naphthalene-1-carboxylic acid fluoride are obtained; boiling point: 132° to 140° C./15 mm Hg; melting point: 85° to 86° C., after recrystallisation from hexane.

EXAMPLE 4

400 g of 1-naphthalenesulphonic acid chloride are reacted with 1,800 ml of hydrogen fluoride and 1,600 ml of carbon tetrachloride at 108° to 110° C. and under 17 bars for 8 hours, analogously to Example 1. Distillation of the batch under reduced pressure gives 396 g of a solid product which consists of 5-trifluoromethyl-1-naphthalenesulphonic acid fluoride and 8-trifluoromethyl-1-naphthalenesulphonic acid fluoride. According to the $F^{19}$ spectrum, the ratio between the two compounds is 65 to 35 (by weight). Pure 5-trifluoromethyl-1-naphthalenesulphonic acid chloride has a melting point of 87° to 88° C. and a boiling point of 140° to 142° C./0.2 mm Hg.

EXAMPLE 5

100 g of 1-nitronaphthalene are reacted in 400 ml of hydrogen fluoride and 400 ml of carbon tetrachloride at 110° C. for 6 hours, analogously to Example 1. After working up the batch by distillation, 90 g of a reaction product which contains 15.7% by weight of 5-trifluoromethyl-1-nitronaphthalene, whilst the remainder consists of unreacted 1-nitronaphthalene, are obtained. This corresponds to 42% of the theoretical yield, relative to 1-nitronaphthalene reacted. The 5-trifluoromethyl-1-nitronaphthalene obtained has a boiling point of 120° C./0.4 mm Hg and a melting point of 107° to 108° C.

EXAMPLE 6

100 g of 9,10-dichloroanthracene are reacted with 400 ml of hydrogen fluoride and 500 ml of carbon tetrachloride at 95° C. and under 14.5 bars for 6 hours, analogously to Example 1. After distilling off the excess hydrogen fluoride and the excess carbon tetrachloride the residue is recrystallized from ethanol. 25 g of 1-trifluoromethyl-9,10-dichloroanthracene of melting point 142° to 143° C. are obtained.

What is claimed is:

1. A process for the preparation of an optionally substituted trifluoromethyl-naphthalene which comprises contacting a compound of the formula

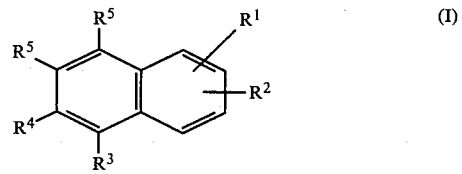

in which
$R^1$ denotes hydrogen, alkyl, aralkyl, aryl, aryloxy, arylthio, polyhalogenoalkoxy, polyhalogenoalkylthio, halogen, nitro, halogenocarbonyl, halogenosulphonyl, alkylsulphonyl or arylsulphonyl, it being possible for the aromatic nuclei contained in the substituents
$R^1$ to be in turn substituted by halogen, alkyl, polyhalogenoalkoxy or polyhalogenoalkylthio,
$R^2$ represents hydrogen, halogen or alkyl and $R^3$, $R^4$, $R^5$ and $R^6$ denote hydrogen, or
$R^3$ and $R^4$ or $R^4$ and $R^5$ in each case together denote a fused-on aromatic ring,
and wherein, in the case where $R^3$ and $R^4$ together form a fused-on aromatic ring,
$R^5$ and $R^6$ independently of one another can also denote, in addition to hydrogen, halogen, nitro, halogenocarbonyl or halogenosulphonyl,
and wherein, in the case where $R^4$ and $R^5$ together form a fused-on aromatic ring,
$R^3$ and $R^6$ independently of one another can also denote, in addition to hydrogen, halogen, nitro, halogenocarbonyl or halogenosulphonyl,
with carbon tetrachloride and hydrogen fluoride at a temperature of 70° to 120° C. and under a pressure of 5 to 30 bars in the absence of copper or a copper compound.

2. A process according to claim 1 wherein a naphthalene of the formula

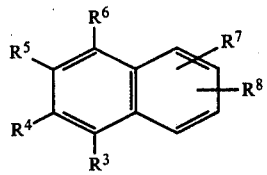

in which
- $R^7$ denotes aryloxy, arylthio, polyhalogenoalkoxy, polyhalogenoalkylthio, halogen, nitro, halogenocarbonyl, halogenosulphonyl, alkylsulphonyl or arylsulphonyl, it being possible for the aromatic nuclei contained in the substituent $R^7$ to be in turn substituted by halogen, alkyl, polyhalogenoalkoxy or polyhalogenoalkylthio,
- $R^8$ represents hydrogen or halogen and
- $R^3$ to $R^6$ have the meaning indicated in claim 1, is employed as the compound of formula (I).

3. A process according to claim 1 wherein a naphthalene of the formula

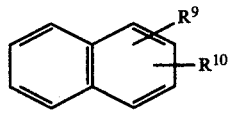

in which
- $R^9$ denotes halogen, nitro, halogenocarbonyl or halogenosulphonyl and
- $R^{10}$ represents hydrogen or halogen, is employed as the compound of formula (I).

4. A process according to claim 1 wherein a naphthalene of the formula

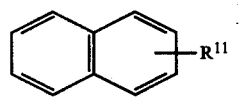

in which
- $R^{11}$ denotes chlorocarbonyl or chlorosulphonyl, is employed as the compound of formula (I).

5. A process according to claim 1 wherein that a compound of the formula

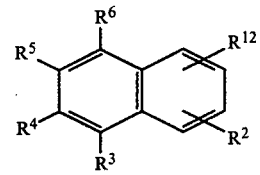

in which
- $R^2$ to $R^6$ have the meaning given in claim 1 and $R^{12}$ denotes chlorine or bromine, is employed as the compound of the formula (I), and the reacted product is then reacted further with hydrogen in the presence of a Raney catalyst and in the presence of an alkaline substance.

6. A process according to claim 1 wherein to remove undesired isomeric reaction products from the resultant reaction mixture the same is contacted with hydrogen in the presence of a hydrogenation catalyst.

7. A process according to claim 6 wherein the contacting with hydrogen is in the presence of a Raney nickel containing catalyst.

8. A process according to claim 6 wherein the contacting with hydrogen is at 20° to 60° C. at 25 to 75 bars hydrogen pressure.

9. A process according to claim 1 wherein the reaction of the compound of formula (I) with carbon tetrachloride and hydrogen fluoride is conducted in the absence of a catalyst.

10. A process according to claim 1, wherein said compound is 1-chloronaphthalene.

11. A process according to claim 1, wherein said compound is 1-naphthalene carboxylic acid chloride.

12. A process according to claim 1, wherein said compound is 1-naphthalene sulphonic acid chloride.

13. A process according to claim 1, wherein said compound is 1-nitronaphthalene.

14. A process according to claim 1, wherein said compound is 9,10-dichloroanthracene.

* * * * *

UNITED STATES PATENT AND TRADEMARK OFFICE
CERTIFICATE OF CORRECTION

PATENT NO. : 4,331,613
DATED : May 25, 1982
INVENTOR(S) : ALBRECHT MARHOLD and ERICH KLAUKE It is certified that error appears in the above-identified patent and that said Letters Patent are hereby corrected as shown below:

Column 4, line 2, "pentabromoethylthio" should read -- pentachloroethylthio --.

Column 8, line 2, "chloride" should read -- fluoride --.

Signed and Sealed this

Seventh Day of December 1982

[SEAL]

Attest:

GERALD J. MOSSINGHOFF

Attesting Officer     Commissioner of Patents and Trademarks